United States Patent
Misner et al.

(10) Patent No.: US 10,830,760 B2
(45) Date of Patent: Nov. 10, 2020

(54) DEVICE FOR RAPID DETECTION OF TUBERCULOSIS-LIPOARABINOMANNAN (TB-LAM) WITH ENHANCED SENSITIVITY

(71) Applicants: General Electric Company, Schenectady, NY (US); TOKITAE LLC, Bellevue, WA (US)

(72) Inventors: Matthew Jeremiah Misner, Delanson, NY (US); Gregory Andrew Grossmann, Halfmoon, NY (US); Cathryn Ellen Olsen, Wilton, NY (US); John Richard Nelson, Clifton Park, NY (US); David Roger Moore, Rexford, NY (US); Paul Michael Smigelski, Jr., Glenville, NY (US); John Thomas Connelly, Seattle, WA (US); Benjamin David Grant, Bellevue, WA (US); Bernhard Hans Weigl, Seattle, WA (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 224 days.

(21) Appl. No.: 15/848,302

(22) Filed: Dec. 20, 2017

(65) Prior Publication Data
US 2019/0187126 A1   Jun. 20, 2019

(51) Int. Cl.
*G01N 33/493* (2006.01)
*C07K 1/22* (2006.01)
(Continued)

(52) U.S. Cl.
CPC ......... *G01N 33/493* (2013.01); *A61B 10/007* (2013.01); *B01D 15/08* (2013.01);
(Continued)

(58) Field of Classification Search
CPC ............ G01N 33/493; G01N 33/5038; G01N 33/569; G01N 33/5695; G01N 2015/1493;
(Continued)

(56) References Cited

U.S. PATENT DOCUMENTS

| | | | |
|---|---|---|---|
| 2,677,372 A * | 5/1954 | Barnish, Jr. | A61J 1/16 604/414 |
| 6,599,691 B1 | 7/2003 | Ralls et al. | |

(Continued)

FOREIGN PATENT DOCUMENTS

| | | | |
|---|---|---|---|
| CN | 203443962 U | 2/2014 | |
| WO | WO-9726007 A1 * | 7/1997 | ............. A61K 39/04 |
| WO | 2016130638 A1 | 8/2016 | |

OTHER PUBLICATIONS

Hunter et al. "Structure and Antigenicity of the Phosphorylated Lipopolysaccharide Antigens from the Leprosy and Tubercle Bacilli" The Journal of Biological Chemistry vol. 261, No. 26, Issue of Sep. 15, pp. 12345-12351, 1986 (Year: 1986).*

(Continued)

*Primary Examiner* — Samuel P Siefke
*Assistant Examiner* — Quocan B Vo
(74) *Attorney, Agent, or Firm* — Fletcher Yoder, P.C.

(57) ABSTRACT

A device for rapid detection of a tuberculosis lipoarabinomannan (TB-LAM) is provided. The device includes a pre-concentrator unit for concentrating the TB-LAM comprising: an ion-exchange medium comprising one or more ligands configured to capture the TB-LAM from the source biological sample, wherein the captured-TB-LAM is eluted from the ion-exchange medium as an eluate comprising a concentrated form of TB-LAM; a cassette; a lateral flow assay unit disposed in the cassette; and an integration unit attached to the pre-concentrator unit and the cassette. The integration unit is configured to operatively couple and (Continued)

de-couple the pre-concentrator unit and the cassette. The pre-concentrator unit and the lateral flow assay unit disposed in the cassette are in a fluidic communication in a coupled form. The device for rapid detection of TB-LAM further comprises a dilutor unit.

22 Claims, 3 Drawing Sheets

(51) Int. Cl.
  B01D 15/08 (2006.01)
  G01N 33/50 (2006.01)
  G01N 33/569 (2006.01)
  B01D 63/02 (2006.01)
  A61B 10/00 (2006.01)
  C12M 1/26 (2006.01)
  G01N 33/558 (2006.01)
  G01N 15/14 (2006.01)

(52) U.S. Cl.
  CPC ............... B01D 63/02 (2013.01); C07K 1/22 (2013.01); C12M 33/14 (2013.01); G01N 33/5038 (2013.01); G01N 33/558 (2013.01); G01N 33/569 (2013.01); G01N 33/5695 (2013.01); A61M 2202/005 (2013.01); A61M 2202/0028 (2013.01); A61M 2202/0071 (2013.01); A61M 2202/0496 (2013.01); G01N 2015/1493 (2013.01)

(58) Field of Classification Search
  CPC ........ G01N 33/558; C07K 1/22; B01D 15/08; B01D 63/02; C12M 33/14; A61M 2202/005; A61M 2202/0496; A61M 2202/0028; A61M 2202/0071; A61B 10/007
  See application file for complete search history.

(56) References Cited

U.S. PATENT DOCUMENTS

| | | | |
|---|---|---|---|
| 6,841,159 B2 | 1/2005 | Simonson | |
| 7,335,480 B2 | 2/2008 | Koulchin et al. | |
| 9,404,923 B2 | 8/2016 | Luke | |
| 2003/0064526 A1* | 4/2003 | Niedbala | B01L 3/5029 436/165 |
| 2004/0059256 A1* | 3/2004 | Perez | A61B 10/0045 600/583 |
| 2005/0026301 A1* | 2/2005 | Petithory | B01L 3/50273 436/180 |
| 2007/0244368 A1* | 10/2007 | Bayloff | A61B 10/0045 600/300 |
| 2009/0148870 A1 | 6/2009 | Ericson | |
| 2009/0320623 A1* | 12/2009 | Matallana-Kielmann | G01N 33/558 73/864.91 |
| 2010/0323343 A1* | 12/2010 | Egan | C12Q 1/6804 435/5 |
| 2011/0097318 A1* | 4/2011 | Gadgil | A61K 9/0019 424/130.1 |
| 2013/0309237 A1* | 11/2013 | Macary | C07K 16/1289 424/137.1 |
| 2014/0377770 A1 | 12/2014 | Bischof et al. | |
| 2015/0260714 A1* | 9/2015 | Achkar | G01N 33/5695 514/2.9 |
| 2016/0256621 A1* | 9/2016 | Toro | A61M 5/14 |
| 2017/0328896 A1* | 11/2017 | Luloh | G01N 33/558 |
| 2019/0038747 A1* | 2/2019 | Pinter | A61K 39/40 |
| 2019/0062812 A1* | 2/2019 | Kampmann | C12Q 1/689 |

OTHER PUBLICATIONS

Hamasur et al. "Rapid diagnosis of tuberculosis by detection of mycobacterial lipoarabinomannan in urine" Journal of Microbiological Methods 45 Ž2001. 41-52 (Year: 2001).*
Sada et al. "Evaluation of Lipoarabinomannan for the Serological Diagnosis of Tuberculosis" Journal of Clinical Microbiology, Dec. 1990, p. 2587-2590 (Year: 1990).*
Sada et al., "Detection of Lipoarabinomannan as a Diagnostic Test for Tuberculosis", Journal of Clinical Microbiology, vol. 30, Issue: 9, pp. 2415-2418, Sep. 1992.
Hamasur et al., "Rapid diagnosis of tuberculosis by detection of mycobacterial lipoarabinomannan in urine", Journal of Microbiological Methods, vol. 45, Issue: 1, pp. 41-52, May 2001.
Lawn et al., "Urine lipoarabinomannan assay for tuberculosis screening before antiretroviral therapy diagnostic yield and association with immune reconstitution disease", AIDS., vol. 23, Issue: 14, pp. 1875-1880, Sep. 10, 2009.
Peter et al., "Urine for the diagnosis of tuberculosis: current approaches, clinical applicability, and new developments", Curr Opin Pulm Med., vol. 16, Issue: 3, pp. 262-270, May 2010.
Lawn et al., "Xpert® MTB/RIF assay: development, evaluation and implementation of a new rapid molecular diagnostic for tuberculosis and rifampicin resistance", Future Microbiol., vol. 6, Issue: 9, pp. 1067-1082, Sep. 2011.
Wood et al., "Lipoarabinomannan in urine during tuberculosis treatment: association with host and pathogen factors and mycobacteriuria", BMC Infect Dis., vol. 12, Issue: 47, pp. 1-11, Feb. 27, 2012.
Lawn et al., "Diagnostic accuracy of a low-cost, urine antigen, point-of-care screening assay for HIV-associated pulmonary tuberculosis before antiretroviral therapy: a descriptive study", Lancet Infect Dis., vol. 12, Issue: 3, pp. 201-209, Mar. 2012.
Lawn SD, "Point-of-care detection of lipoarabinomannan (LAM) in urine for diagnosis of HIV-associated tuberculosis: a state of the art review", BMC Infect Dis., pp. 1-12, Apr. 26, 2012.
Peter et al., "Diagnostic accuracy of a urine lipoarabinomannan strip-test for TB detection in HIV-infected hospitalised patients", Eur Respir J., vol. 40, Issue: 5, pp. 1211-1220, Nov. 2012.
Sakamuri et al., "Association of lipoarabinomannan with high density lipoprotein in blood: implications for diagnostics", Tuberculosis (Edinb)., vol. 93, Issue: 3, pp. 301-307, May 2013.
Nicol et al., "Urine lipoarabinomannan testing for diagnosis of pulmonary tuberculosis in children: a prospective study", Lancet Glob Health., vol. 2, Issue: 5, pp. 278-284, May 2014.
Nakiyingi et al., "Diagnostic accuracy of a rapid urine lipoarabinomannan test for tuberculosis in HIV-infected adults", J Acquir Immune Defic Syndr., vol. 66, Issue: 3, pp. 270-279, Jul. 1, 2014.
Mianabe et al., "Point-of-care lateral flow assays for tuberculosis and cryptococcal antigenuria predict death in HIV infected adults in Uganda", PLoS One., vol. 9, Issue: 7, pp. 1-7, Jul. 7, 2014.
Kerkhoff et al., "Prognostic value of a quantitative analysis of lipoarabinomannan in urine from patients with HIV-associated tuberculosis", PLoS One., vol. 9, Issue: 7, pp. 1-7, Jul. 30, 2014.
Lawn et al., "Massive diagnostic yield of HIV-associated Tuberculosis using rapid urine diagnostic assays in South Africa", Program and Abstracts of the Conferences on Retroviruses and Opportunistic Infections (CROI), 2014.
Peter et al., "A Trial of the Urine LAM Strip Test for TB Diagnosis Amongst Hospitalized HIV-infected Patients (LAMRCT)", A service of the U.S. National Institutes of Health, Dec. 2015.
Lawn et al., "Rapid diagnosis of TB in HIV-positive in-patients with M. tuberculosis bacteraemia in sub-Saharan Africa", Int J Tuberc Lung Dis., vol. 19, Issue: 12, pp. 1557-1559, Dec. 2015.
"The use of lateral flow urine lipoarabinomannan assay (LF-LAM) for the diagnosis and screening of active tuberculosis in people living with HIV", World Health Organization, Geneva, 2015.
Lawn et al., "Rapid urine-based screening for tuberculosis to reduce AIDS-related mortality in hospitalized patients in Africa (the STAMP trial): study protocol for a randomised controlled trial", BMC Infectious Diseases, pp. 2-11, 2016.

* cited by examiner

DEVICE FOR RAPID DETECTION OF TUBERCULOSIS-LIPOARABINOMANNAN (TB-LAM) WITH ENHANCED SENSITIVITY

This application relates generally to a device for detection of tuberculosis-lipoarabinomannan (TB-LAM) of a source biological sample. In a particular aspect, the application relates to a device for rapid diagnostic testing of TB-LAM associated with tuberculosis.

BACKGROUND

A rapid detection method of analytes or target biomolecules performed by employing a rapid diagnostic test (RDT) is relatively less time consuming and less labor intensive as compared to conventional methods. Rapid diagnostic tests (RDTs) have been used for detection of various infectious diseases. The RDTs are suitable for preliminary and/or emergency medical screening, for example, for use in medical facilities with limited resources, and offer a useful alternative to microscopy in situations where a reliable microscopic diagnosis facility is not available or is not immediately available. RDTs also allow point of care (POC) testing in primary care. RDTs can be performed independent of laboratory equipment by minimally trained personnel, and are adapted to deliver instant results. RDTs provide results within 2 hours to 10 minutes. An RDT employs a dipstick or cassette format for testing a biological specimen, such as a urine sample. For testing, the biological specimen collected from a patient is applied to a sample pad on a test strip (or card) of the RDT dipstick or cassette along with certain reagents. Depending on the type of test that is being conducted, after a determined period of time, presence or absence of specific bands in a test strip window indicates whether a certain antigen of interest is present in the biological specimen, such as a patient's sample. Generally, a drop of the biological specimen is added to the RDT device through a sample well, and then a buffer is usually added through a buffer well. The buffer carries the biological specimen along the length of the RDT device.

Among major infectious diseases, tuberculosis is different in that it lacks accurate rapid point-of-care diagnostic tests. Inefficient detection methods and lack of timely treatment of tuberculosis are major causes of failure to control the spread of tuberculosis. Laboratory based diagnostic tests for detecting tuberculosis are currently available, however these tests need multiple investigations over a period of weeks or months. Multiple new diagnostic tests have recently been developed for detecting active tuberculosis, latent tuberculosis infection, and identifying drug-resistant strains of Mycobacterial tuberculosis. However, a robust point-of-care test with high accuracy, greater accessibility, reduced cost and complexity is desirable for early detection of tuberculosis. Further, an effective method for diagnosing extra-pulmonary mycobacterial tuberculosis infections, which are on the rise in HIV-positive subjects, is also highly desirable.

Prior methods for detecting surface polysaccharides (LAM) using different body fluids, such as serum, urine or sputum, have been investigated, but have proven ineffective. For example, prior studies with urine sample required extensive sample processing and manipulation, rendering such methodologies complex and cumbersome, specifically in the field.

BRIEF DESCRIPTION

In some embodiments, a device for detection of tuberculosis lipoarabinomannan (TB-LAM) of a source biological sample is provided. The device comprises a pre-concentrator unit for concentrating the TB-LAM, a cassette, a lateral flow assay unit disposed in the cassette, and an integration unit attached to the pre-concentrator unit and the cassette. The pre-concentrator unit comprises an ion-exchange medium comprising one or more ligands configured to capture the TB-LAM from the source biological sample, wherein the captured-TB-LAM is eluted from the ion-exchange medium as an eluate comprising a concentrated form of TB-LAM. The integration unit is configured to operatively couple and de-couple the pre-concentrator unit and the cassette, wherein the pre-concentrator unit and the lateral flow assay unit disposed in the cassette are in a fluidic communication in a coupled form.

In some other embodiments, a device for detection of tuberculosis lipoarabinomannan (TB-LAM) of a source biological sample is provided. The device, comprises a dilutor unit configured to dilute the source urine sample and form a diluted urine sample, a pre-concentrator unit for concentrating the TB-LAM, a cassette; a lateral flow assay unit disposed in the cassette; and an integration unit attached to the pre-concentrator unit and the cassette. The pre-concentrator unit comprises an ion-exchange medium comprising one or more ligands configured to capture the TB-LAM from the source biological sample, wherein the captured-TB-LAM is eluted from the ion-exchange medium as an eluate comprising a concentrated form of TB-LAM. The integration unit is configured to operatively couple and de-couple the pre-concentrator unit and the cassette, wherein the pre-concentrator unit and the lateral flow assay unit disposed in the cassette are in a fluidic communication in a coupled form.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
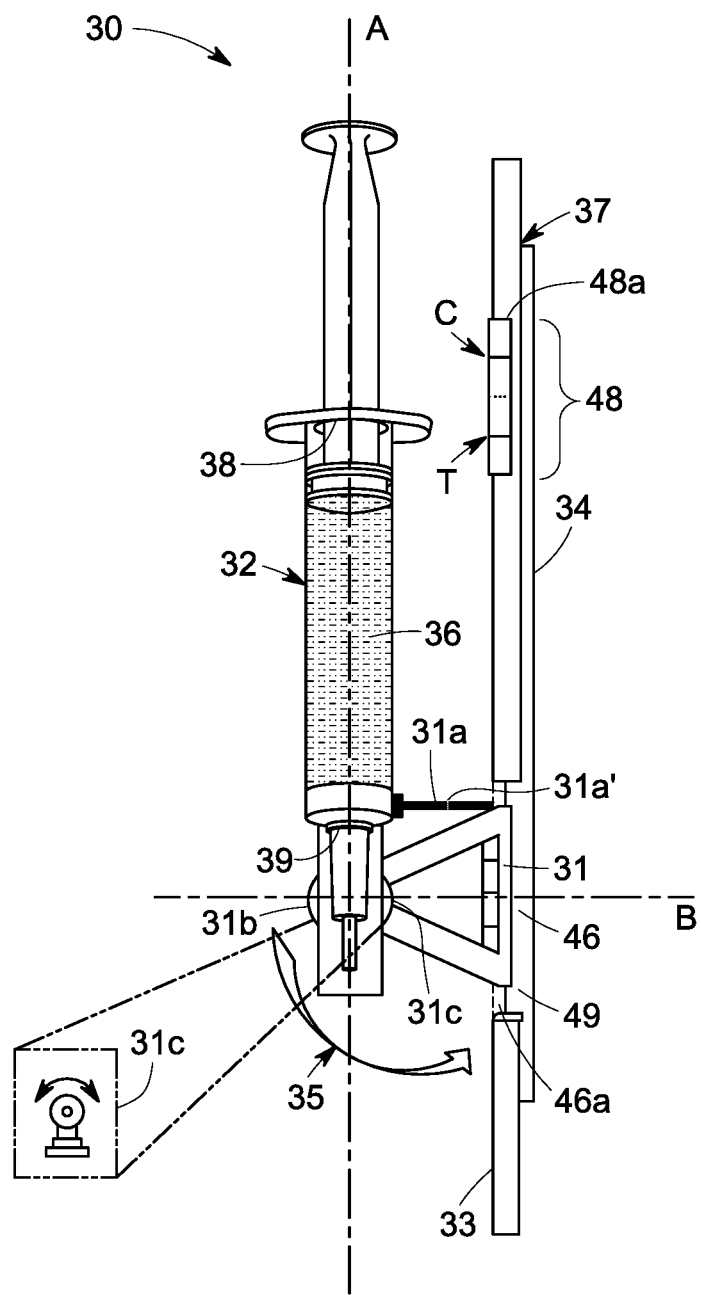
FIG. 1 is a schematic drawing of a perspective view of one embodiment of a device in de-coupled form for rapid detection of a tuberculosis lipoarabinomannan (TB-LAM).

A device associated with a rapid detection method is provided, which overcomes difficulties in the currently known methods and devices by providing enriched mycobacterial antigens (e.g., tuberculosis-lipoarabinomannan) from a biological sample collected from a subject. The biological sample enriched with tuberculosis-lipoarabinomannan (TB-LAM) further enhances sensitivity of the rapid diagnostic tests. In accordance with certain embodiments, the device for detection of TB-LAM from a source biological sample employs rapid diagnostic tests (RDTs). Rapid diagnostic testing devices produce a visible band on a rapid diagnostic testing device by binding an antigen (e.g., TB-LAM) using antibodies, such as dye-labeled antibodies. For rapid diagnostic testing, in one aspect, an antibody binds to the antigen, such as a tuberculosis biomarker TB-LAM. The resultant TB-LAM-antibody complex may further be bound by a dye-labeled secondary antibody or a conjugate particle-coupled secondary antibody forming a visible band (test line) in a result window of the rapid diagnostic testing device.

To more clearly and concisely describe the subject matter of the disclosed application, the following definitions are provided for specific terms, which are used in the following description and the appended embodiments. Throughout the specification, exemplification of specific terms should be considered as non-limiting examples.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "rapid diagnostic test" or RDT refers to a device or a test of a biological sample, which can be carried out at the point of care to obtain fast diagnosis. Rapid diagnostic testing devices employ rapid diagnostic tests that are medical diagnostic tests that are quick and easy to perform and can be carried out even in the absence of laboratory techniques such as microscopy, enzyme-linked immunosorbent assay (ELISA) or polymerase chain reaction (PCR). By way of a non-limiting example, rapid diagnostic testing for tuberculosis typically require about 30 minutes from the time of sample collection to the time of obtaining a result. It should be noted that time required for a rapid diagnostic testing depends on variables, such as the type of sample, the amount of sample, the nature of the analyte, and the like.

Embodiments of a device for detection of tuberculosis lipoarabinomannan (TB-LAM) of a source biological sample are presented herein. In some embodiments, the device is employed for rapid diagnostic testing of a TB-LAM. The device is compatible with equipment-free, point of care analyte (TB-LAM)-separation and detection process. For example, the device provides rapid diagnostic testing by immunochromatographic separation and detection of TB-LAM from a biological sample, such as a urine sample. Improved sensitivity of a rapid diagnostic testing is desired, however, an early detection of tuberculosis (TB) is made complicated by frequent false positive tests and a huge variability of band intensity particularly in the very low concentration range of the TB-LAM.

According to embodiments of the present technique, a device for detection of TB-LAM of a source biological sample, such as a urine sample, is provided. The device broadly includes a) a pre-concentrator unit; b) an immune based assay unit, and c) an integration unit. In detail, the device for detection of TB-LAM of a source biological sample comprises a pre-concentrator unit, a cassette, a lateral flow assay (LFA) unit disposed in the cassette, and an integration unit attached to the pre-concentrator unit and the cassette. The pre-concentrator unit is used for concentrating the TB-LAM in the source biological sample. The pre-concentrator unit comprises an ion-exchange medium comprising one or more ligands configured to capture the TB-LAM from the source biological sample. The captured-TB-LAM is eluted from the ion-exchange medium as an eluate comprising a concentrated form of TB-LAM. The integration unit is configured to operatively couple and de-couple the pre-concentrator unit and the cassette. In operation, the pre-concentrator unit and the lateral flow assay unit disposed in the cassette are in a fluidic communication.

A cassette and a LFA unit disposed in the cassette formed an immune based assay unit, which is coupled or decoupled to the pre-concentrator unit through the integration unit. The LFA unit comprises an antibody capable of binding to the concentrated form of the TB-LAM received from the pre-concentrator unit, where the pre-concentrator unit is operatively coupled to the cassette holding the LFA unit to allow loading of the concentrated form of the TB-LAM to the LFA unit. In some embodiments, the device further comprises a dilutor unit.

The sensitivity of the immuno-chromatographic antigen-detection tests generally rely on concentration of the TB-LAM present in the source biological sample. To achieve a desired sensitivity of detection, a concentrated form of the TB-LAM is generated by using the device by capturing and concentrating TB-LAM by the pre-concentrator unit before loading to the LFA unit of the device. Sensitivity of the immunochromatographic antigen-detection tests further rely on binding efficiency of an antigen (here, TB-LAM) to an antibody and the stability of the antigen-antibody complex. To provide a more concentrated form of TB-LAM to an antibody, a more concentrated form of the TB-LAM generated by the device and the eluate is subsequently flown to the LFA unit of the device, where the LFA unit comprises an antibody to form a stable TB-LAM-antibody complex. This two-step process of concentrating the TB-LAM and loading the biological sample containing concentrated TB-LAM to the LFA unit for detection of TB-LAM is effected by this single device without any human intervention.

In one or more embodiments, the TB-LAM is a complex lipopolysaccharide antigen composed of mannose and arabinose residues forming a highly branched and complex structure. In some embodiments, if the TB-LAM is detected in the biological sample (such as the urine sample), it is concluded that the biological sample is collected from a TB-positive subject. LAM is a virulence factor associated with *Mycobacterium tuberculosis*, the bacteria responsible for TB. The bacterium survives in the human reservoir by undermining host resistance and acquired immune responses by inhibiting T-cell proliferation and macrophage microbicidal activity. It is believed that as LAM outflows into the circulation in an active TB infection and passes through the kidneys, LAM can be detected in the urine sample of a TB patient reflecting the level of mycobacterial burden. TB-LAM is typically found in human urine at very low concentration levels, such as picogram levels. The RDTs are prone to give false positive results to identify TB-LAM at such low concentration levels. To achieve desired results using RDTs, in certain embodiments, a concentrated form of TB-LAM is needed.

Referring to FIG. 1, a device 30, in accordance with one embodiment, comprises a pre-concentrator unit 32 and an immune based assay unit 37. The immune based assay unit 37 comprises a cassette 33 which contains a lateral flow assay (LFA) unit 34. The integration unit 31 is configured to couple the pre-concentrator unit 32 and the cassette 33. Further, the integration unit 31 is configured to orient the concentrator unit 32 in two or more positions with respect to the cassette 33. By way of example, when the device 30 is not in use, the integration unit 31 is configured such that the pre-concentrator unit 32 and the cassette 33 containing the LFA unit 34 are positioned in an operatively de-coupled form. In such a configuration, there is no fluidic communication present between the pre-concentrator unit 32 and the LFA unit 34 disposed in the cassette 33. Further, in operation, the fluidic communication is established between the pre-concentrator unit 32 and the LFA unit 34 disposed in the cassette 33 via the integration unit 31. In particular, the integration unit 31 facilitates movement, such as rotation, of the pre-concentrator unit 32 such that the LFA unit 34 and the pre-concentrator unit 32 are in fluidic communication with one another.

In some embodiments, the pre-concentrator unit 32 comprises a column, a syringe, a channel, a filter unit, or a conduit. The pre-concentrator unit 32 includes an input channel or inlet 38 for loading the source biological sample to the device 30. The pre-concentrator unit 32 further includes an output channel or outlet 39 for flowing the eluate out of the pre-concentrator unit 32. The pre-concentrator unit 32 comprises an ion-exchange medium 36 for concentrating the TB-LAM. The ion-exchange medium 36 is used to concentrate the TB-LAM present in a source biological sample and to provide a concentrated form of the TB-LAM to the LFA unit 34 for downstream detection of TB-LAM.

The ion-exchange medium 36 comprises one or more ligands, wherein the ligands comprise cationic- or anionic-exchange ligands. The anionic-exchange ligands include, but are not limited to, quaternary ammonium ion, and dimethyl aminoethyl (DMAE) groups. In some embodiments, the ion-exchange medium 36 includes an ion exchange material, an ion-exchange membrane, or an ion-exchange matrix. The ion-exchange medium 36 may be disposed on the pre-concentrator unit 32 for concentrating the TB-LAM. In one embodiment, the ion-exchange medium is an anion-exchange membrane, for example Q+ membrane (GE Healthcare Life Sciences, Pittsburgh, Pa., US). Further, the anion exchange membrane is easily adaptable to the pre-concentrator unit 32 and to the immune-based assay unit 37 that includes a LFA unit 34. The anion exchange membrane is also easy to dispose to the pre-concentrator unit 32 in the field-able applications. In some embodiments, an anion-exchange membrane specific for capturing TB-LAM may be used to concentrate the TB-LAM before loading the eluate comprising the concentrated form of the TB-LAM to the device 30 for detection of TB-LAM of a source biological sample. For example, an amine-based ion-exchange membrane is employed to concentrate TB-LAM from the urine sample. In such embodiments, the amine-based ion-exchange membrane is used for concentrating TB-LAM, which significantly improves a signal for detection of TB. In some embodiments, by using the ion-exchange medium 36, a concentration of the TB-LAM in the eluate may be increased to 2× to 25× compared to a concentration of the TB-LAM in the source biological sample. For example, by using a Q+ anion exchange membrane for concentrating the TB-LAM, the TB-LAM is concentrated by 15× and 25×.

In alternative embodiments, the ion exchange medium 36 may comprise an anion-exchange resin. In such embodiments, a column chromatography containing an anion exchange resin is used to capture and concentrate the TB-LAM. For example, Capto™Adhere resin (GE Healthcare Life Sciences, Pittsburgh, Pa., US) or Capto™Adhere ImpRes resin (GE Healthcare Life Sciences, Pittsburgh, Pa., US) may be selected as the anion-exchange resin to capture TB-LAM. In the anion-exchange resin chromatography, a larger volume of buffer may be required to elute the biomolecule compared to the volume of buffer required for anion-exchange membrane. Further, an efficient packing of the resin and refrigeration of the resin may be required for anion exchange resin.

The cassette 33 may have a channel where the LFA unit 34 is inserted. The cassette 33 includes a sample well 46a for receiving a source biological sample or a diluted biological sample containing a concentrated form of TB-LAM received from the pre-concentrator unit 32. The sample well 46a of the cassette 33 positioned relative to the sample receiving zone 46 of the LFA unit 34. The detection zone 48 of the LFA unit 34 is positioned relative to the result window or detection window 48a of the cassette so that the test line T and control line C of the LFA unit 34 may be visualized by a user of the assay. The cassette 33 comprises one or more raised area of different size, shape and position to hold the LFA unit (assay strip) 34 in an appropriate angle and position for visualization through the result window 48a. The cassette 33 may further comprise a buffer well adjacent to the sample well 46a.

Depending on the embodiment, a cassette 33 can be fabricated from materials selected for features such as weight, cost, durability, and chemical interactions with the interior features of the device. In some embodiments, the cassette 33 may be made of a polymer, a metal, a glass, or a combination thereof. For example, the cassette housing is fabricated from a plastic material. In some other example, the cassette 33 is fabricated by a hydrophobic material. In some example embodiments, the cassette 33 is fabricated from a hydrophobic plastic material.

The LFA unit 34 comprises an antibody to bind the concentrated form of the TB-LAM antigen received from the pre-concentrator unit 32. In some embodiments, the LFA unit comprises a sample receiving zone 46 and a detection zone 48. The sample receiving zone 46 may further be referred to as a "sample application pad" or a "sample pad." The sample receiving zone 46 is operatively coupled to the pre-concentrator unit 32 such that the concentrated form of the TB-LAM is received from the pre-concentrator unit 32 by the sample receiving zone 46. The sample receiving zone 46 may be present on a fiber glass, quartz, or a cellulose substrate for receiving the biological sample comprising a concentrated form of the TB-LAM. Optionally, a conjugate zone 49 is disposed adjacent to and upstream of the sample receiving zone 46, wherein the conjugate zone comprises a conjugate particle for binding with the TB-LAM. A concentrated form of the TB-LAM is received by the sample receiving zone 46 from the pre-concentrator unit 32. The detection zone 48 is disposed adjacent to and downstream of the sample receiving zone 46. The detection zone 48 comprises at least one antibody for capturing the TB-LAM. The detection zone may be constructed on a nitrocellulose membrane. The detection zone 48 comprises a test region or test line "T." In some embodiments, the test region is a sub-zone of the detection zone 48 where antibody is deposited. The TB-LAM binds to the antibodies disposed on the test line T forming TB-LAM-antibody complexes. The TB-LAM-antibody complexes may further bound to conjugate particle-coupled antibodies on the test line T, forming a visible test line in the result window 48a of the cassette 33. In some other embodiments, the LFA unit includes dye-labeled antibodies to bind TB-LAM and produce a visible band on the test line T in the result window 48a of the cassette 33. The presence of the TB-LAM is visually detected by change in color of the test region T in the detection zone 48. The detection zone 48 further comprises a control region or control line "C." One or more binding agents having affinity towards the conjugate particles deposited on the control region C, these binding agents do not exhibit any affinity towards the TB-LAM. The control line C gives information on integrity of the conjugate particle-coupled antibody and fluidics of the LFA unit 34, as the control line C typically comprises a species-specific anti-immunoglobulin antibody i.e., secondary antibody specific for the conjugate particle-coupled antibody. The control line C gives information on integrity of the conjugate particle-coupled antibody and fluidics of the LFA unit. On binding of the TB-LAM to the TB-LAM-specific antibody, such as reporter-linked TB-LAM specific antibody, a signal may be generated. In case of exceeding the signal intensity over a pre-determined threshold value, it indicates presence of TB-LAM in the biological sample over a certain concentration level. The higher signal intensity is advantageous for detection of TB-LAM because generally RDTs rely on visually detected changes in color of the test region T on an immune-based assay unit. A faint color change is not visually detectable and could lead to a false negative result on the RDT device.

The integration unit 31 is employed as a mechanical fastener between the pre-concentrator unit 32 and the cassette 33. The integration unit 31 further comprises a fastener 31a for locking the pre-concentrator unit 32 and the cassette 33 in a parallel configuration. The fastener 31a may be de-coupled, for example by breaking the fastener 31a, from one of the pre-concentrator unit 32 and the cassette 33 for realigning the pre-concentrator unit 32 or the cassette 33 with respect to one another. In one example, the fastener 31a may be broken to realign the pre-concentrator unit 32 from a parallel configuration with the cassette 33 by rotating the pre-concentrator unit 32 with respect to the cassette 33. In some embodiments, the fastener 31a may be de-coupled from one of the pre-concentrator unit 32 and the cassette 33, for example by breaking the fastener 31a along a perforated area 31a'. The integration unit 31 further comprises a clamp 31b for holding the pre-concentrator unit 32. The integration unit 31 also comprises a lever 31c capable of rotating the pre-concentrator unit 32. The lever 31c is attached to the integration unit 31, further the lever 31c is present adjacent to the clamp 31b. The lever 31c is configured to rotate the pre-concentrator unit 32 such that the pre-concentrator unit 32 is positioned at an appropriate position and orientation with reference to the LFA unit 34 of the cassette 33 for enabling operation of the device 30. The pre-concentrator unit 32 is configured to rotate with reference to an axis A and can orient along an axis B. The pre-concentrator unit 32 may be rotated clockwise or anticlockwise with reference to the axis A. In some embodiments, the pre-concentrator unit 32 may be rotated anticlockwise along a path of rotation 35 towards the LFA unit 34. In the illustrated embodiment of FIG. 1, the pre-concentrator unit 32 is rotated by 90 degrees and to align along the axis B.

The integration unit 31 is configured to align the pre-concentrator unit 32 and the cassette 33 such that an angle between the pre-concentrator unit 32 and the cassette 33 is between 0 degree to 180 degrees. In some embodiments, the integration unit 31 is configured to align the pre-concentrator unit 32 and the cassette 33 such that an angle between the pre-concentrator unit 32 and the cassette 33 is 0 degree. In such embodiments, the pre-concentrator unit 32 and the cassette 33 containing the LFA unit 34 are positioned parallelly to each other. The parallel configuration of the device 30 is referred to herein as the "de-coupled" form of the device 30. The parallel configuration of the device 30 is compact and easy to package. In some other embodiments, the integration unit 31 is configured to align the pre-concentrator unit 32 and the cassette 33 such that the angle between the pre-concentrator unit and the cassette is 90 degrees, which is a "coupled form" (FIG. 2).

Figure 2:
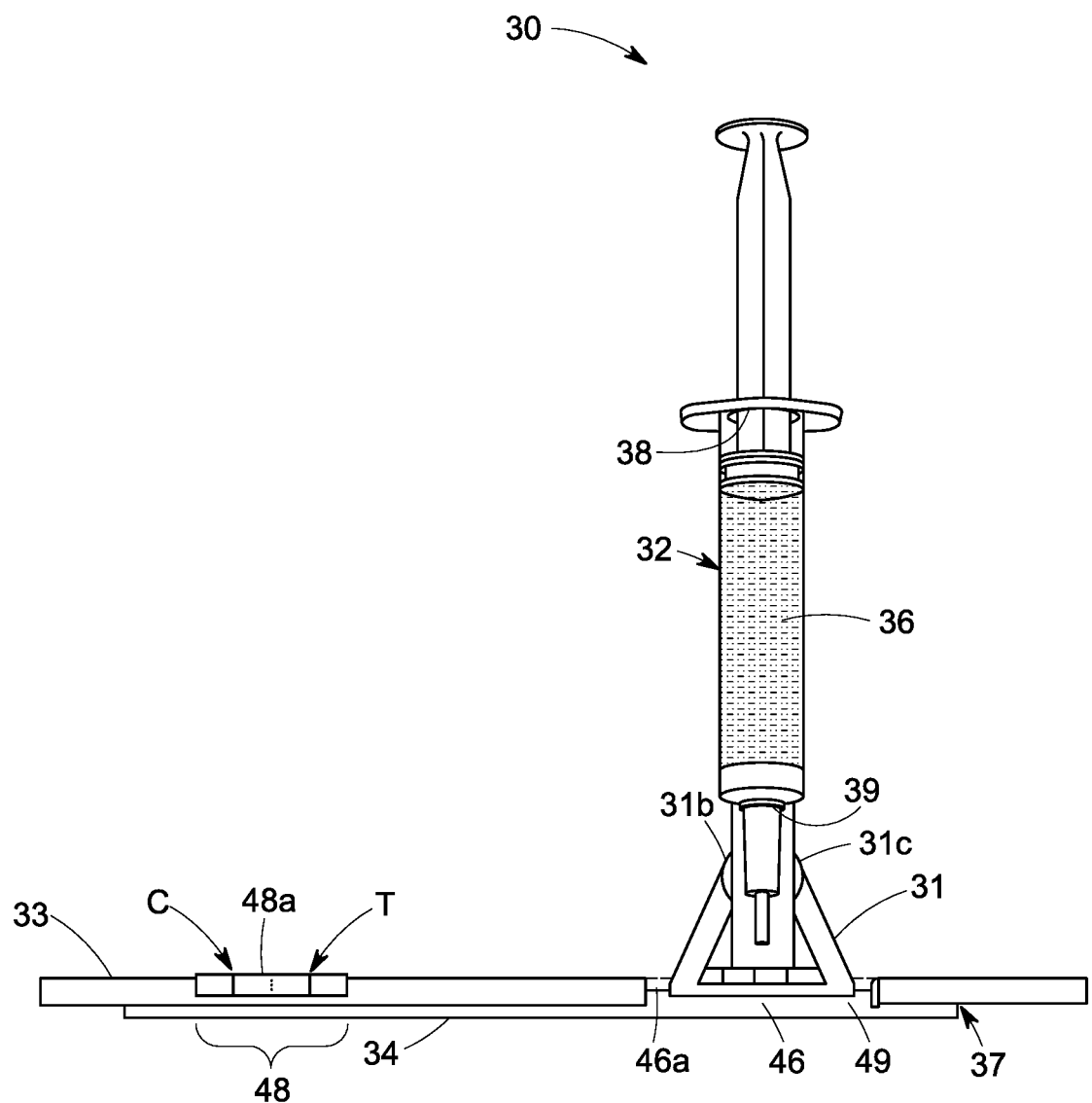
FIG. 2 is a schematic drawing of a perspective view of one embodiment of a device in coupled form for rapid detection of a TB-LAM.

Referring now to FIG. 2, which is a "coupled form" of the device 30, in accordance with one embodiment, the integration unit 31 is configured to operatively couple the pre-concentrator unit 32 and the cassette 33. In such embodiments of the device 30, the pre-concentrator unit 32 and the cassette 33 containing the LFA unit 34 may be in a physical contact with one another. In such embodiments, the pre-concentrator unit 32 and the LFA unit 34 are coupled or connected by a mechanical fastener, such as, integration unit 31. The integration unit 31 is attached to both the pre-concentrator unit 32 and the cassette 33 containing the LFA unit 34. When the device 30 is in use or in operating condition, the integration unit 31 is configured such that the pre-concentrator unit 32 and the cassette 33 containing the LFA unit 34 are operatively coupled to each other. In such configuration, a fluidic communication is established between the pre-concentrator unit 32 and the LFA unit 34 disposed in the cassette 33.

Figure 3:
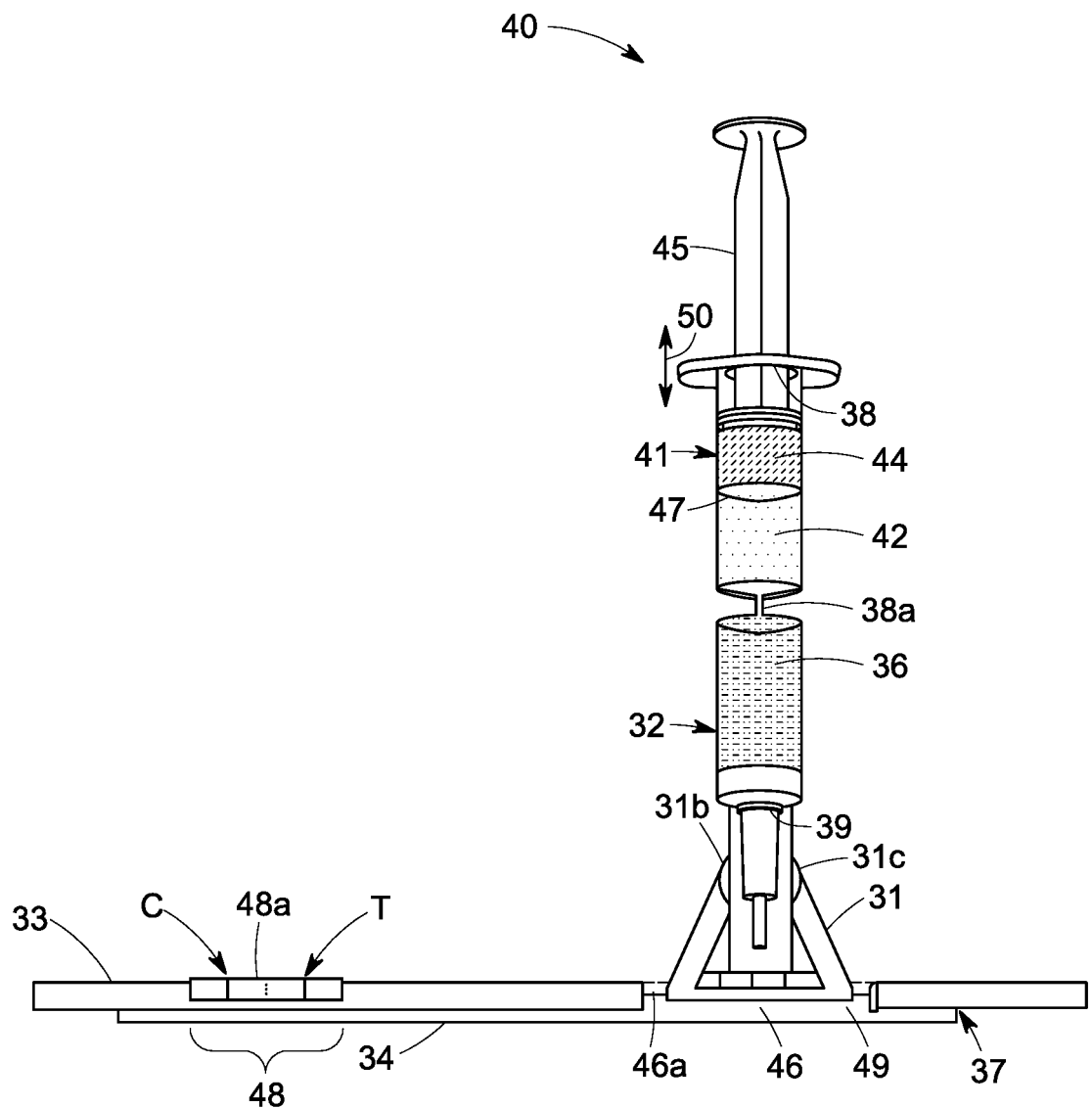
FIG. 3 is a schematic drawing of a perspective view of another embodiment of a device in coupled form for rapid detection of a TB-LAM.

FIG. 3 illustrates the coupled form of a device 40. In the coupled form of the device 30, 40 (FIG. 3) the pre-concentrator unit 32 may be positioned to the LFA unit 34 in any angle between 0 degree and 180 degrees. In some embodiments, the pre-concentrator unit 32 is positioned perpendicularly to the LFA unit 34 of the cassette 33. Although not illustrated, in some embodiments of the coupled form (FIGS. 2, 3) of the device 30, 40 the pre-concentrator unit 32 and the cassette 33 are align such that an angle between the pre-concentrator unit and the cassette may be less than 90 degrees. In some other embodiments of the coupled form of the device 30, 40, the angle between the pre-concentrator unit 32 and the LFA unit 34 is in a range from 30 degrees to 120 degrees.

As noted, the pre-concentrator unit 32 is operatively coupled to the LFA unit 34 to allow loading of the concentrated form of the antigen from the pre-concentrator unit 32 to the LFA unit 34. The pre-concentrator unit 32 and the lateral flow unit 34 are operatively coupled or connected at least by a fluidic communication. The output channel or outlet 39 facilitates a fluid flow from the pre-concentrator unit 32 to the LFA unit 34 during operation of the device 30 (FIG. 2), 40 (FIG. 3). For example, a urine sample flows from the pre-concentrator unit 32 to the LFA unit 34, which provides a fluidic communication under the operating conditions of the device 30, 40.

The pre-concentrator unit 32 receives at least a portion of the diluted or undiluted biological sample through an inlet 38. In some embodiments, the source biological sample may be introduced in the device 30 without any dilution. In these embodiments, the source biological sample is contacted with the ion-exchange medium 36 without any dilution. In such embodiments, a salt-tolerant anion-exchange medium, for example, an anion exchange membrane containing primary amine may be used. The pre-concentrator unit 32 comprises an ion-exchange medium 36 for rapid separation of undesired materials from the source biological sample and forms at least partially purified biological sample comprising concentrated form of the TB-LAM. The eluate comprising the concentrated form of the TB-LAM is directed to the LFA unit 34 through an outlet 39 of the pre-concentrator unit 32. The pre-concentrator unit 32 is operatively coupled to the LFA unit 34 to allow loading of the concentrated form of the TB-LAM from the pre-concentrator unit 32 to the LFA unit 34. The output channel or outlet 39 helps in flowing the eluate out from the pre-concentrator unit 32 to the LFA unit 34 disposed in the cassette 33, when the device is in an operating condition. The eluate comprises a concentrated form of the TB-LAM.

Referring now to FIG. 3, a device 40, in accordance with one embodiment, comprises a dilutor unit 41 in addition to the components of the pre-concentrator unit 32 and an immune based assay unit 37. The device 40 may be employed in embodiments where it is desirable to dilute the source biological sample in the device 40 before contacting the source biological sample with the ion exchange medium 36. The integration unit 31 is configured to operatively couple (FIG. 3) or de-couple (not shown for device 40, similar to device 30 in FIG. 1) the pre-concentrator unit 32 and the cassette 33 containing the LFA unit 34, when the device 40 is in use, or the device 40 is not in use, respectively.

The dilutor unit 41 includes a dilutor 42 and an input chamber 44. The input chamber 44 is configured to receive the source biological sample. The dilutor unit 41 and the pre-concentrator unit 32 are operatively coupled to each other. In some embodiments, the dilutor unit 41 is coupled to the pre-concentrator unit 32 via a diluted sample inlet 38a. The dilutor unit 41 is operatively coupled to the LFA unit 34 via a fluidic connection through the pre-concentrator unit 32. The dilutor 42 may be a mixing chamber or mixing vessel where the dilution of the source biological sample takes place by mixing the source biological sample with an appropriate buffer solution. In some embodiments, the dilutor 42 may be pre-filled with a buffer solution as per requirement of the desired dilution. In some embodiments, the required volume of buffer is added to the dilutor 42 after addition of the source biological sample to the input chamber. The input chamber 44 is a chamber for receiving the source biological sample and feeding the source biological sample to the dilutor 42 in a controlled manner using a plunger 45. In some embodiments, the input chamber 44 is a syringe having a plunger. The plunger 45 may be linearly pulled and pushed along the inside of the chamber 44 in directions represented by arrows 50, allowing the chamber 44 (e.g., syringe) to receive and discharge the source biological sample through a discharge outlet 47 located at the front end (opposite end of the plunger 45) of the input chamber 44 such as the syringe. The discharge outlet 47 may be an orifice, a membrane, or a filter through which the source biological sample may pass through and enter the dilutor 42.

The dilutor unit 41 is configured to dilute the source biological sample between 2× to 6× dilution compared to the source biological sample to form a diluted biological sample. In some embodiments, the source biological sample (e.g., urine) comprising the TB-LAM is diluted at least by 2× to form a diluted biological sample before contacting the source biological sample to the ion-exchange medium 36. In some other embodiments, the source biological sample (e.g., urine) comprising the TB-LAM is diluted by 4× to form a diluted biological sample before contacting the source biological sample to the ion-exchange medium 36. For example, a urine sample collected from a subject is diluted by 4× with a buffer to reduce salinity of the urine sample. By reducing the salinity of the urine sample, binding efficiency of the TB-LAM of the urine sample to the ion-exchange medium may be enhanced. The source biological sample may be a urine sample collected from a TB patient for detection of TB-LAM using immuno-chromatographic antigen-detection tests.

The device is used for rapid detection of a TB-LAM by concentrating the TB-LAM to increase sensitivity of the rapid diagnostic test, followed by loading the concentrated form of the TB-LAM to a LFA unit 34 for immuno-chromatographic antigen-detection tests for rapid diagnostic testing of the TB-LAM. A source biological sample may be collected from a patient suffering from an infectious disease, such as tuberculosis (TB). In a non-limiting example, the source biological sample may be a urine sample collected from a TB patient for detection of TB-LAM. The source biological sample is diluted in the dilutor 41 of a device 40, if the diluted sample is not used directly for applying to the device. The source biological sample comprising the TB-LAM is applied to the device through the inlet 38. After applying to the device 30, 40, the diluted biological sample is contacted with an ion-exchange medium 36 and the TB-LAM if present in the biological sample, is captured by the ligands of the ion exchange medium 36. The captured TB-LAM is typically eluted from the ion-exchange medium 36 as an eluate. The eluate comprising the concentrated form of the TB-LAM in the solution is loaded to the LFA unit 34 for rapid diagnostic testing of the TB-LAM.

As noted, the LFA unit comprises an antibody, wherein the antibody is specific to the antigenic moiety of the TB-LAM. In one or more embodiments, the antibody is a monoclonal antibody. In some other embodiments, the antibody is a polyclonal antibody. In some examples, the polyclonal antibody is an affinity purified polyclonal antibody. Due to high structural complexity and variability of TB-LAM, a complex spectrum of antigenic epitopes is generated. The use of affinity purified polyclonal antibody allows to cover the full spectrum of antigenic specificities potentially associated with LAM present in clinical samples. The enriched antibodies may be raised for a specific epitope of LAM in an environment which maintains its antigenic activity. In one or more embodiments, the TB-LAM-specific antibody used for LFA unit is a reporter-linked TB-LAM-specific antibody or a labeled antibody. As used herein, "labeled antibody" includes an antibody coupled to an enzyme or a substrate. In some examples, an enzyme is capable of changing color on exposure to a substrate. In some examples, a substrate is capable of changing color on exposure to a reagent (such as an enzyme). As such, the antibody may be labeled with a dye, a metal particle (e.g., gold), a compound capable of producing chemiluminescence or fluorescence. In alternative embodiments, the antibody may be attached to a magnetic bead, a cellulose bead, a polymeric bead labeled with a dye, an affinity probe, and the like.

The conjugate particle may include colloidal gold, a colored particle, a fluorescent probe, a paramagnetic particle (such as paramagnetic monodisperse latex particle), or combinations thereof. The lateral flow unit 34 may further include alternative conjugate reporters such as cellulose nanobeads (CNB), magnetic beads, fluorescence tags, chemiluminescence molecules, or various shapes of gold nanoparticles including nanospheres, nanorods, and nanoshells. Such alternative conjugate reporters are contemplated within the scope of embodiments presented herein. The conjugate particle is conjugated to one of the components of the biological sample, a component of the lateral flow assay strip (such as binding agent), or a biomolecule such as a protein. The protein may be an antigen or an antibody, depending on a format of the assay.

The devices presented herein enable enhanced detection of TB-LAM in a source biological sample by increasing the concentration of the TB-LAM in the biological sample compared to the concentration of TB-LAM in a sample used for commercially available RDT devices. In some embodiments, a volume of a urine sample generally employed for the device may be in a range from about 2.5 ml to 10 ml. The TB-LAM present in such high volume of the urine sample is more than is present in a smaller volume of the urine sample. By using the pre-concentrator unit, the TB-LAM is concentrated and eluted from the pre-concentrator unit in 70-100 μL volume. The ability of a device to process larger sample volume by using a pre-concentrator unit indicates that a larger amount of TB-LAM reaches the LFA unit while using the device of the present Application, which results in improving the signal intensity of the device. Advantageously, in the present Application, the device generates ~20× concentrated TB-LAM (or antigen), which allows enhanced intensity signals while using lower volume of the concentrated samples thereby providing improved sensitivity of the point of care (POC) test. The device ensures generating a concentrated form of TB-LAM and loading the concentrated form of the TB-LAM to the LFA unit comprising TB-LAM-specific antibody to generate better signal intensity compared to the commercially available RDTs. The device is also effective for diagnosing extra-pulmonary mycobacterial infections for a subject having co-infection of TB and human immune deficiency virus (HIV).

In one or more embodiments, the source biological sample comprises urine, blood, feces, sweat, saliva, mucous, milk, semen, serum, plasma, sputum, tears, tissue, or combinations thereof. For detecting surface polysaccharides (LAM) using different body fluids such as serum, urine or sputum have been investigated, however, none of these body fluids were found to be effective for diagnosing extra-pulmonary mycobacterial infections such as those on the rise in HIV-positive subjects. Embodiments of the present method overcome such difficulties by providing enriched mycobacterial antigens TB-LAM in a wide range of sample types from a subject. In some embodiments, the sample types include unprocessed, or undiluted urine sample.

While only certain features of the invention have been illustrated and described herein, many modifications and changes will occur to those skilled in the art. It is, therefore, to be understood that the appended embodiments are intended to cover all such modifications and changes as fall within the scope of the invention.

The invention claimed is:

1. A device for detection of tuberculosis lipoarabinomannan (TB-LAM) of a source biological sample, comprising:
   a pre-concentrator unit for concentrating the TB-LAM comprising:
      an ion-exchange medium comprising one or more ligands configured to capture the TB-LAM from the source biological sample, wherein the captured-TB-LAM is eluted from the ion-exchange medium as an eluate comprising a concentrated form of TB-LAM;
   a cassette;
   a lateral flow assay unit disposed in the cassette; and
   an integration unit attached to the pre-concentrator unit and the cassette at a pivot point,
   wherein the integration unit comprises a clamp to hold the pre-concentrator unit, wherein the integration unit is coupled to a lever that is adjacent to the clamp, and wherein the cassette is configured to transition from an uncoupled position to a coupled position via rotation of the integration unit about the pivot point relative to the pre-concentrator unit, wherein the pre-concentrator unit and the lateral flow assay unit disposed in the cassette are in a fluidic communication in the coupled position.

2. The device of claim 1, further comprising a dilutor unit configured to dilute the source biological sample between 2× to 6× dilution compared to the source biological sample to form a diluted biological sample.

3. The device of claim 2, wherein the dilutor unit is configured to dilute the source biological sample to 4× dilution compared to the source biological sample to form the diluted biological sample.

4. The device of claim 2, wherein the dilutor unit and the pre-concentrator unit are operatively coupled to each other.

5. The device of claim 1, wherein the integration unit is configured to align the pre-concentrator unit and the cassette such that an angle between the pre-concentrator unit and the cassette is between 0 degree to 180 degrees.

6. The device of claim 5, wherein the integration unit is configured to align the pre-concentrator unit and the cassette such that the angle between the pre-concentrator unit and the cassette is 0 degree.

7. The device of claim 5, wherein the integration unit is configured to align the pre-concentrator unit and the cassette such that the angle between the pre-concentrator unit and the cassette is 90 degrees.

8. The device of claim 1, wherein the ion-exchange medium comprises an ion exchange membrane, an ion exchange resin, an ion-exchange matrix, an ion exchange filter, or combinations thereof.

9. The device of claim 1, wherein the one or more ligands comprise anionic ligands.

10. The device of claim 9, wherein the anionic ligands are selected from quaternary ammonium ions, dimethyl aminoethyl (DEAE) groups, or a combination thereof.

11. The device of claim 1, wherein the pre-concentrator unit comprises a column, a syringe, a channel, a filter unit, or a conduit.

12. A device for rapid diagnostic testing of a source urine sample comprising tuberculosis lipoarabinomannan (TB-LAM), comprising:
   a dilutor unit configured to dilute the source urine sample and form a diluted urine sample;
   a pre-concentrator unit configured to concentrate the TB-LAM from the diluted urine sample, comprising:
      an ion-exchange medium comprising one or more ligands configured to capture the TB-LAM from the source urine sample, wherein the captured-TB-LAM is eluted from the ion-exchange medium as an eluate comprising a concentrated form of TB-LAM;
   a cassette;
   a lateral flow assay unit disposed in the cassette; and
   an integration unit attached to the pre-concentrator unit and the cassette, wherein the integration unit comprises a swivel connector coupled to the pre-concentrator unit such that rotation of the pre-concentration unit relative to the cassette causes at least a portion of the pre-concentrator unit to move away from the cassette to transition from an uncoupled position to a coupled position, and
   wherein the cassette is configured to transition from the uncoupled position to the coupled position via rotation of the swivel connector to cause the integration unit to move relative to the pre-concentrator unit, and wherein the integration unit operatively provides a fluidic communication from the pre-concentrator unit to the lateral flow assay unit disposed in the cassette when the pre-concentrator unit and the cassette are coupled to each other.

13. The device of claim 12, wherein the integration unit is configured to align the pre-concentrator unit and the cassette such that an angle between the pre-concentrator unit and the cassette is 0 degree.

14. The device of claim 12, wherein the integration unit is configured to align the pre-concentrator unit and the cassette such that an angle between the pre-concentrator unit and the cassette is 90 degrees.

15. The device of claim 12, wherein the ion-exchange medium comprises an ion exchange membrane, an ion exchange resin, an ion-exchange matrix, an ion exchange filter, or combinations thereof.

16. The device of claim 12, wherein the one or more ligands comprise anionic ligands.

17. The device of claim 16, wherein the anionic ligands comprise quaternary ammonium ions, dimethyl aminoethyl (DEAE) groups, or a combination thereof.

18. The device of claim 12, wherein the lateral flow assay unit comprises one or more TB-LAM specific antibodies.

19. The device of claim 18, wherein the one or more TB-LAM specific antibodies are reporter-linked.

20. The device of claim 12, wherein the dilutor unit is configured to dilute the source urine sample between 2× to 6× dilution compared to the source urine sample to form the diluted urine sample.

21. The device of claim 1, wherein the integration unit is rotatably attached to the pre-concentrator unit and the cassette at the pivot point, and wherein the pre-concentrator unit is configured to rotate from the uncoupled position to the coupled position relative to the cassette.

22. The device of claim 1, wherein the pivot point is a fulcrum configured to rotate such that the integration unit and the cassette are configured to move relative to the pre-concentrator unit.

* * * * *